(12) United States Patent
Amano et al.

(10) Patent No.: US 10,561,826 B2
(45) Date of Patent: Feb. 18, 2020

(54) CATHETER INSERTION DEVICE

(71) Applicant: Becton, Dickinson and Company, Franklin Lakes, NJ (US)

(72) Inventors: Shuichi Amano, Bethlehem, PA (US); Russell Cole, River Vale, NJ (US)

(*) Notice: Subject to any disclaimer, the term of this patent is extended or adjusted under 35 U.S.C. 154(b) by 153 days.

(21) Appl. No.: 15/304,699

(22) PCT Filed: Apr. 23, 2015

(86) PCT No.: PCT/US2015/027364
§ 371 (c)(1),
(2) Date: Oct. 17, 2016

(87) PCT Pub. No.: WO2015/164650
PCT Pub. Date: Oct. 29, 2015

(65) Prior Publication Data
US 2017/0043133 A1 Feb. 16, 2017

Related U.S. Application Data

(60) Provisional application No. 61/983,980, filed on Apr. 24, 2014.

(51) Int. Cl.
*A61M 25/06* (2006.01)
*A61M 5/142* (2006.01)
*A61M 5/158* (2006.01)

(52) U.S. Cl.
CPC .... *A61M 25/0606* (2013.01); *A61M 25/0612* (2013.01); *A61M 5/14248* (2013.01);
(Continued)

(58) Field of Classification Search
CPC ......... A61M 2005/14252; A61M 2005/14256; A61M 2005/1426; A61M 2005/1585;
(Continued)

(56) References Cited

U.S. PATENT DOCUMENTS 5,527,288 A * 6/1996 Gross ................ A61M 5/14248
604/140
7,455,663 B2 * 11/2008 Bikovsky ............ A61M 5/1413
604/240

(Continued)

FOREIGN PATENT DOCUMENTS

JP 2006-525046 A 11/2006
JP 2010/531692 A 9/2010
(Continued)

*Primary Examiner* — Shefali D Patel
(74) *Attorney, Agent, or Firm* — Dickinson Wright PLLC

(57) ABSTRACT

A catheter insertion device, including a housing having a base (504, 604, 704), a flexible beam (510, 610, 710) movably disposed within the housing, an insertion needle (514, 614) connected with the beam, and a holder (518, 618, 718) movably disposed within the housing and movably connected with the insertion needle. The device also includes a catheter (522, 622, 722) connected with the holder to displace therewith, the catheter surrounding at least a portion of the insertion needle, and an actuator button (502, 602, 702) movably connected to the housing and configured to flex the beam upon actuation, thereby displacing the insertion needle and the catheter to an extended position in which respective distal portions of the insertion needle and the catheter extend outside the housing through the base.

17 Claims, 17 Drawing Sheets

(52) U.S. Cl.
CPC ............ *A61M 2005/14252* (2013.01); *A61M 2005/1585* (2013.01)

(58) Field of Classification Search
CPC .. A61M 2005/1586; A61M 2025/0175; A61M 25/0606; A61M 25/0612; A61M 25/0631; A61M 5/14248; A61M 2005/14284; A61M 2005/1583
See application file for complete search history.

(56) References Cited

U.S. PATENT DOCUMENTS

| | | | |
|---|---|---|---|
| 2005/0203461 A1* | 9/2005 | Flaherty | A61M 5/14248 604/131 |
| 2008/0009805 A1 | 1/2008 | Ethelfeld | |
| 2010/0286615 A1* | 11/2010 | Gyrn | A61M 5/158 604/164.04 |
| 2012/0316506 A1 | 12/2012 | Sonderegger et al. | |

FOREIGN PATENT DOCUMENTS

| | | |
|---|---|---|
| WO | WO-9513838 A1 | 5/1995 |
| WO | WO-2004098683 A1 | 11/2004 |
| WO | WO-2008024810 A2 | 2/2008 |

* cited by examiner

CATHETER INSERTION DEVICE

CROSS-REFERENCE TO RELATED APPLICATION

This application claims priority under 35 USC § 119(e) from U.S. Provisional Patent Application Ser. No. 61/983,980 filed on Apr. 24, 2014, the disclosure of which is incorporated herein by reference in its entirety.

FIELD OF THE INVENTION

The present invention relates to medical devices, and more particularly, to medical devices with a catheter insertion mechanism.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

To minimize the height of the insertion mechanism, conventional insertion mechanisms are generally configured to insert the cannula at an acute angle from the surface of the skin, e.g. 30-45 degrees. However, it is generally preferable to insert the cannula perpendicular or close to the perpendicular from the surface of the skin since this would require the minimum length of cannula insertion. In other words, with the minimum length of cannula being inserted into the user's skin, the user can experience greater comfort and fewer complications, such as premature kinking of the cannula.

The main problem with configuring the insertion mechanism to insert the cannula perpendicular to the surface of the skin is that this may likely increase the overall height of the insertion mechanism, and therefore the patch pump, itself. For instance, U.S. Pat. No. 7,909,791 discloses a stand-alone insertion device for infusion sets that utilize various linkages, gears and springs to automatically insert a cannula vertically or perpendicularly into the user's skin. However, incorporating such a device into a patch pump would not only add considerably bulk, complexity and cost, but would greatly increase the height of the patch pump.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, to reduce the overall height of the device the insertion mechanism is incorporated into, such as a patch pump.

SUMMARY OF EMBODIMENTS OF THE INVENTION

It is an aspect of the present invention to provide a patch pump in which a user is only required to perform a single operation to both insert a soft catheter and retract an introducer needle.

The foregoing and/or other aspects of the present invention are achieved by providing a catheter insertion device, including a housing having a base, a flexible beam movably disposed within the housing, an insertion needle connected with the beam, and a holder movably disposed within the housing and movably connected with the insertion needle. The device also includes a catheter connected with the holder to displace therewith, the catheter surrounding at least a portion of the insertion needle; and an actuator button movably connected to the housing and configured to flex the beam upon actuation, thereby displacing the insertion needle and the catheter to an extended position in which respective distal portions of the insertion needle and the catheter extend outside the housing through the base.

The foregoing and/or other aspects of the present invention are also achieved by providing a method of inserting a cannula disposed on a carrier about an insertion needle connected to a beam disposed inside a medical device housing. The method includes deflecting the beam by displacing an actuator button relative to the housing until the catheter and the insertion needle reach an extended position outside the housing, and the carrier locks to the housing.

The foregoing and/or other aspects of the present invention are also achieved by providing a catheter insertion device, including a housing having a base, a flexible beam movably disposed within the housing, an insertion needle connected with the beam, and a holder movably disposed within the housing and movably connected with the insertion needle. The device also includes a catheter connected with the holder to displace therewith, the catheter surrounding at least a portion of the insertion needle; and an actuator button movably connected to the housing and configured to flex the beam upon actuation, thereby displacing the insertion needle and the catheter to an extended position in which respective distal portions of the insertion needle and the catheter extend outside the housing through the base. The actuator button is configured to, upon the insertion needle and the catheter reaching the extended position, continue to travel and further flex the beam. The beam is configured to, subsequent to the insertion needle and the catheter reaching the extended position and the further flexure, disengage from the actuator button and return to an initial beam position, thereby withdrawing the insertion needle from the extended position and ensuring full insertion of the catheter prior to withdrawal of the insertion needle.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
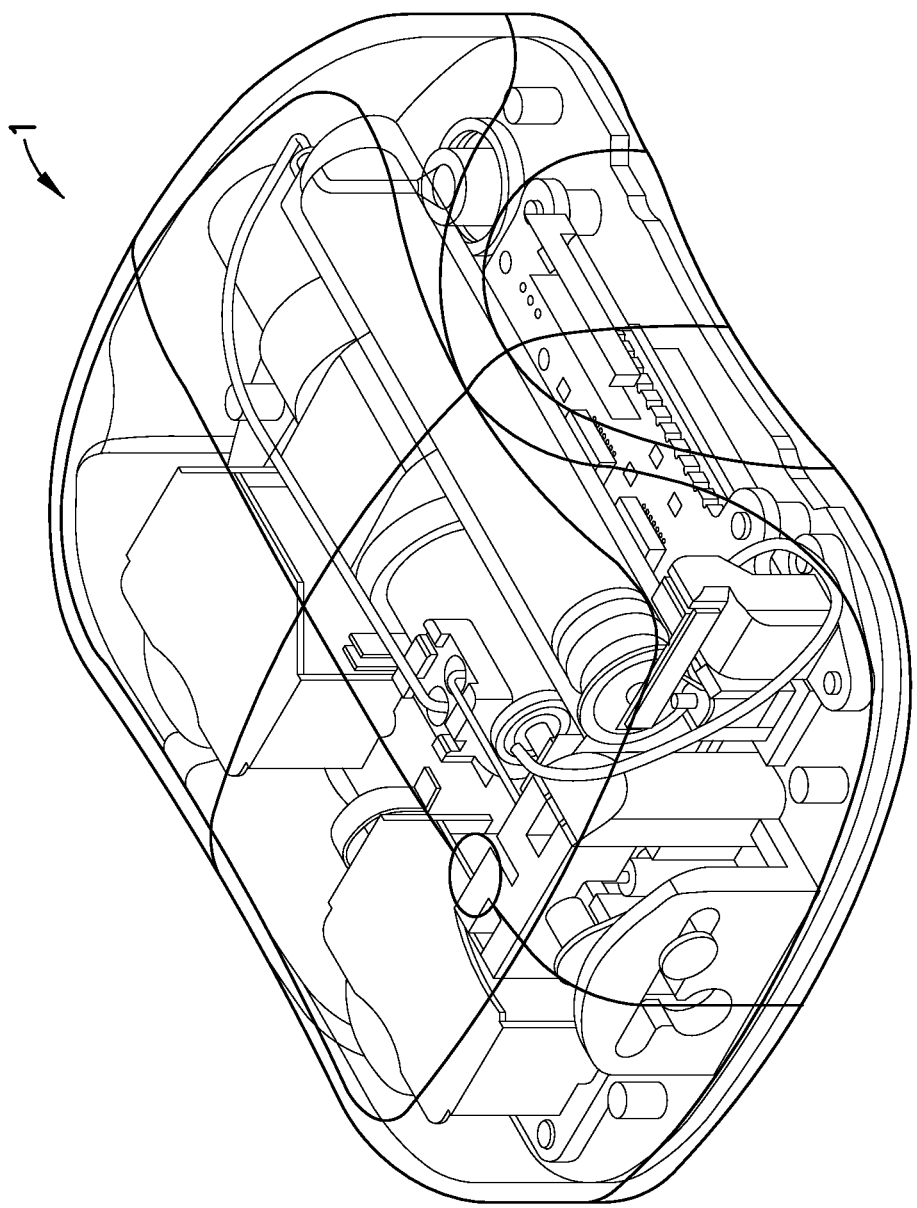
FIG. 1 is a perspective view of a patch pump incorporating a low-profile cannula insertion device, illustrated with a transparent cover for clarity.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 2:
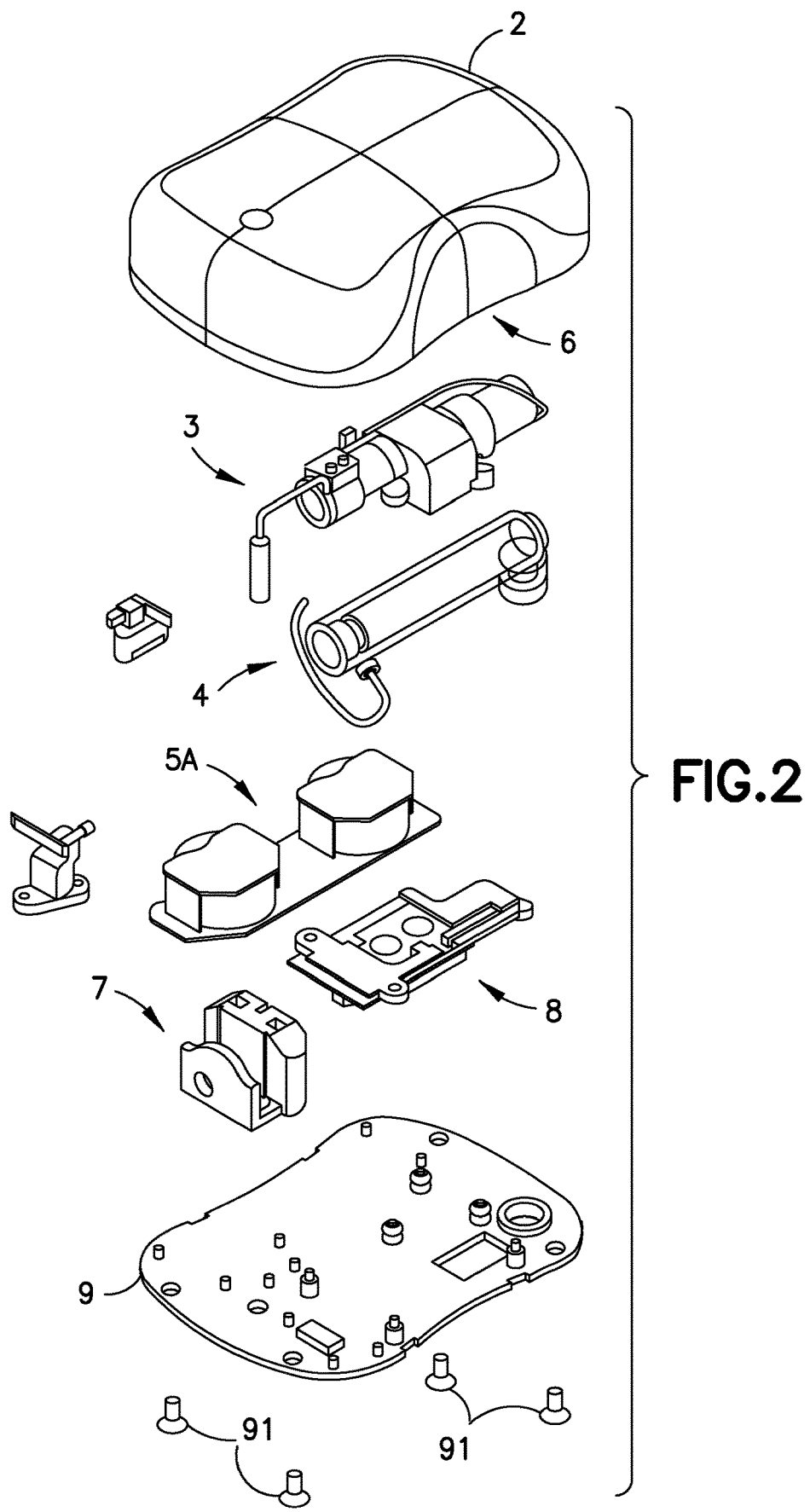
FIG. 2 is an exploded view of the various components of the patch pump of FIG. 1, illustrated with a cover.

FIG. 1 is a perspective view of an exemplary embodiment of a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 3:
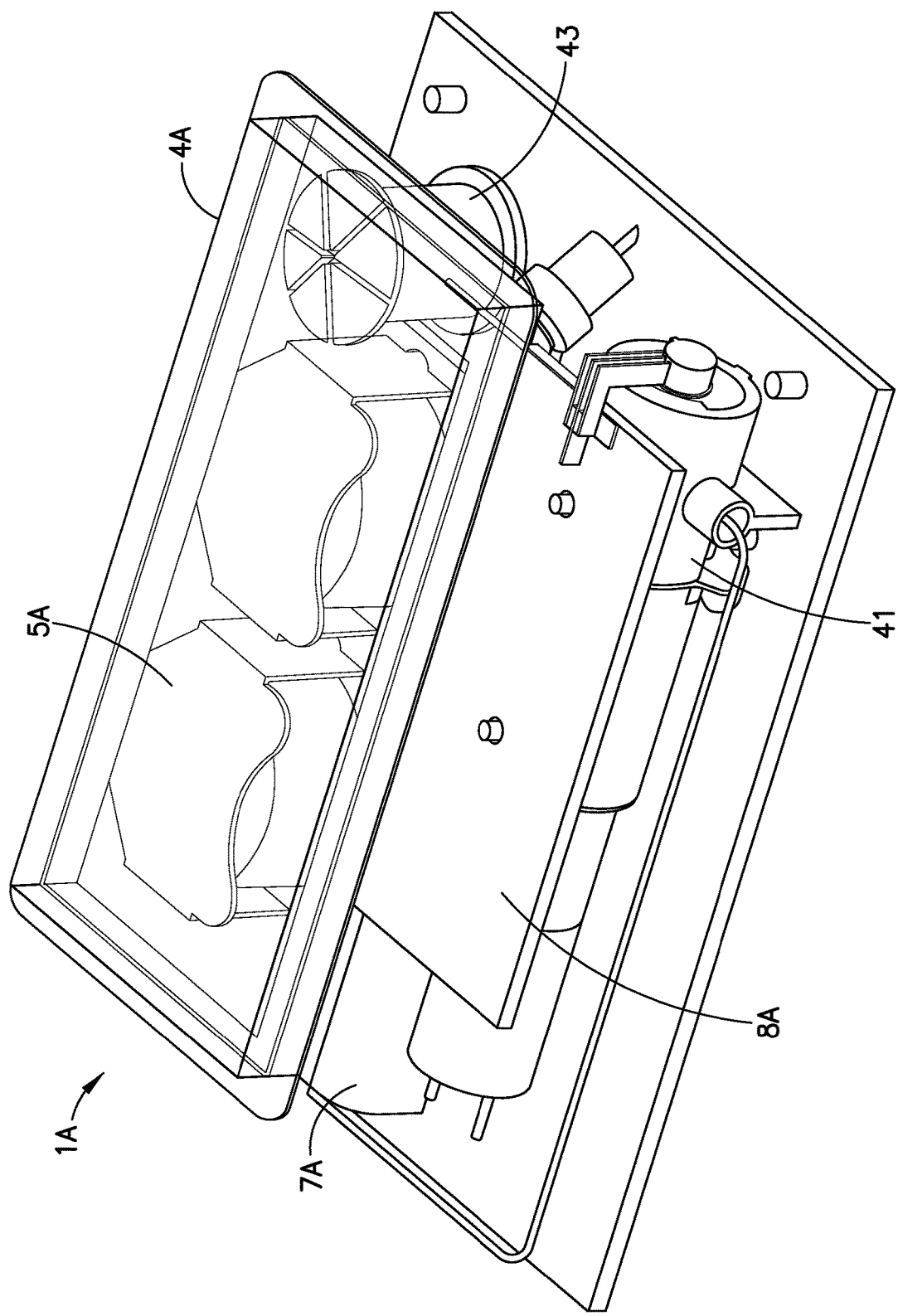
FIG. 3 is a perspective view of an alternative design for a patch pump having a flexible reservoir, illustrated without a cover.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
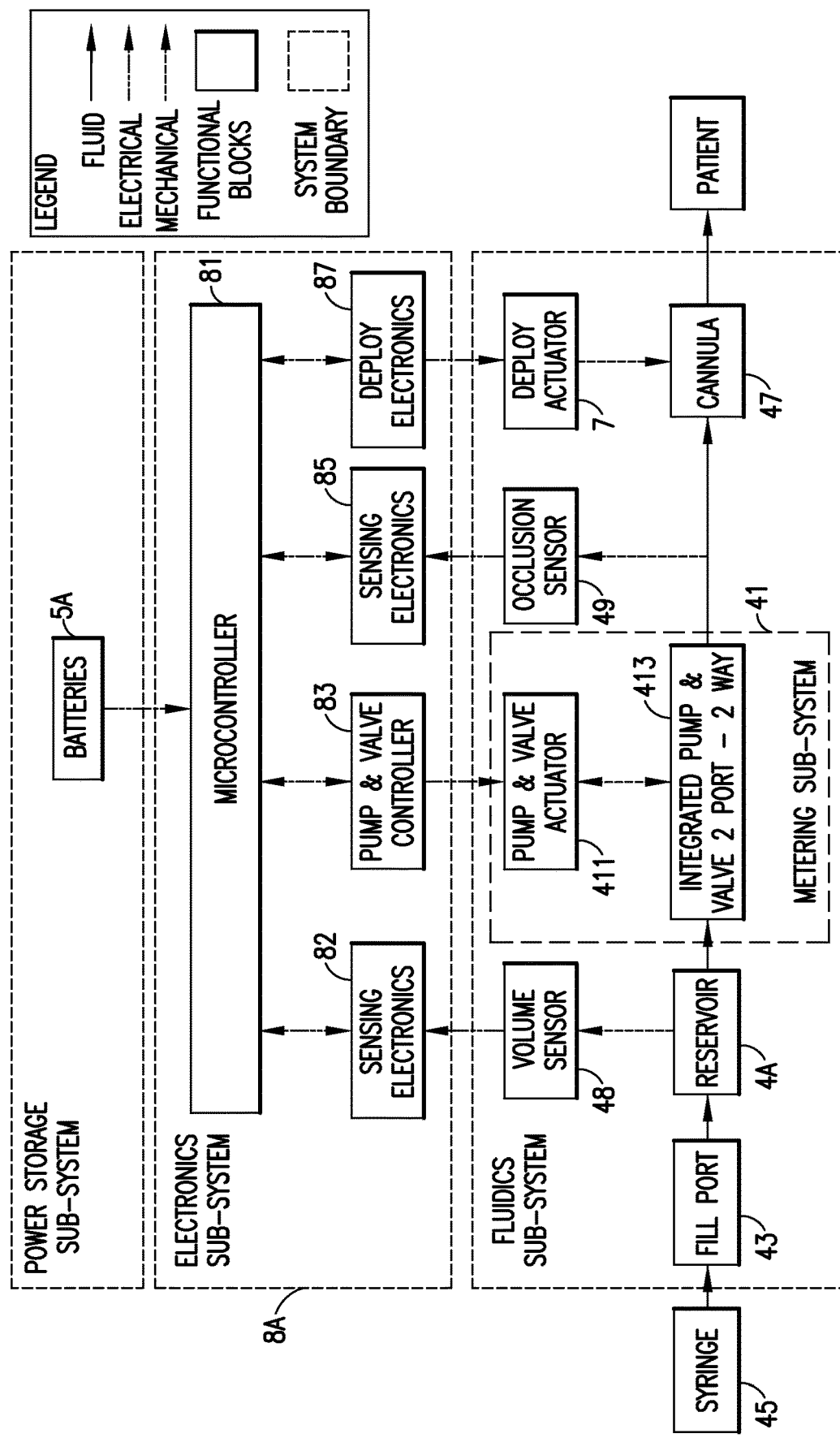
FIG. 4 is a patch-pump fluidic architecture and metering sub-system diagram of the patch pump of FIG. 3.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87, that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

Figure 5:
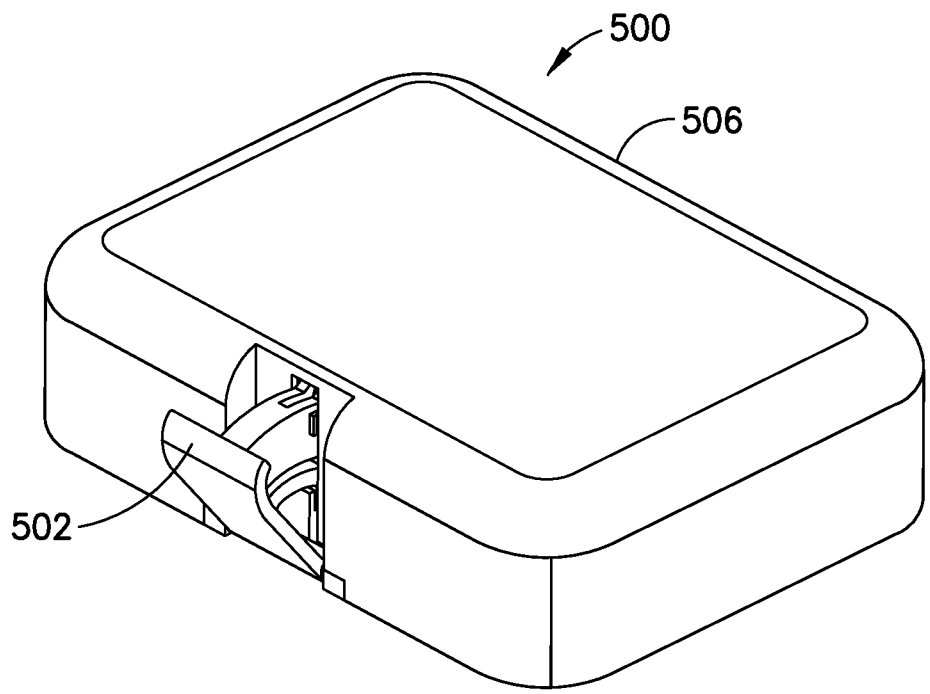
FIGS. 5 and 6 are perspective views of a patch pump in respective pre-actuated and actuated states in accordance with an embodiment of the present invention.
Figure 6:
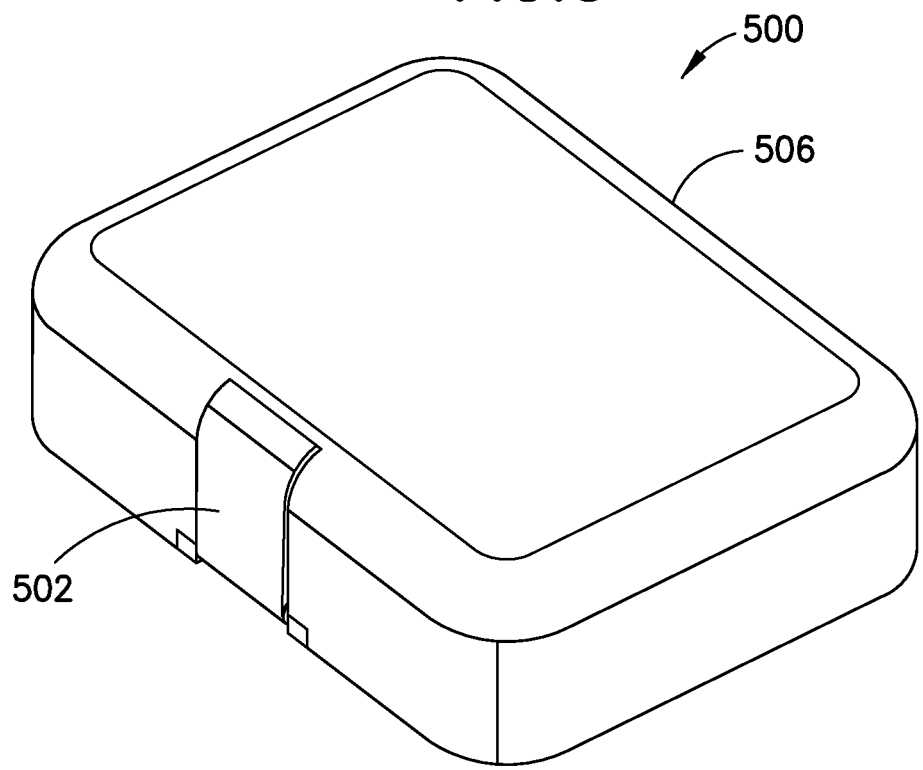

In accordance with an embodiment of the present invention, FIG. 5 is a perspective view of a patch pump 500 in a pre-actuated state, and FIG. 6 is a perspective view of the patch pump 500 in an actuated state. The patch pump 500 includes a side-actuated, manually powered, catheter insertion and retraction mechanism. Briefly, this mechanism is used to insert a catheter and an introducer needle into a patient's body. A user other than a medicament recipient (for example, a health care professional) can use the device 500 because the patient can be a human or an animal. For brevity, the term "user" will be employed to refer to a patient or other user.

The introducer needle is manually inserted and automatically retracted and the catheter remains in the body. To actuate the insertion and retraction mechanism, the user pushes inward on a button on the side of the device. The introducer needle is retracted by the expansion of a flexible plastic beam that is compressed during the insertion stage. The introducer needle remains partially inside the catheter to provide an uninterrupted fluid path.

Figure 7:
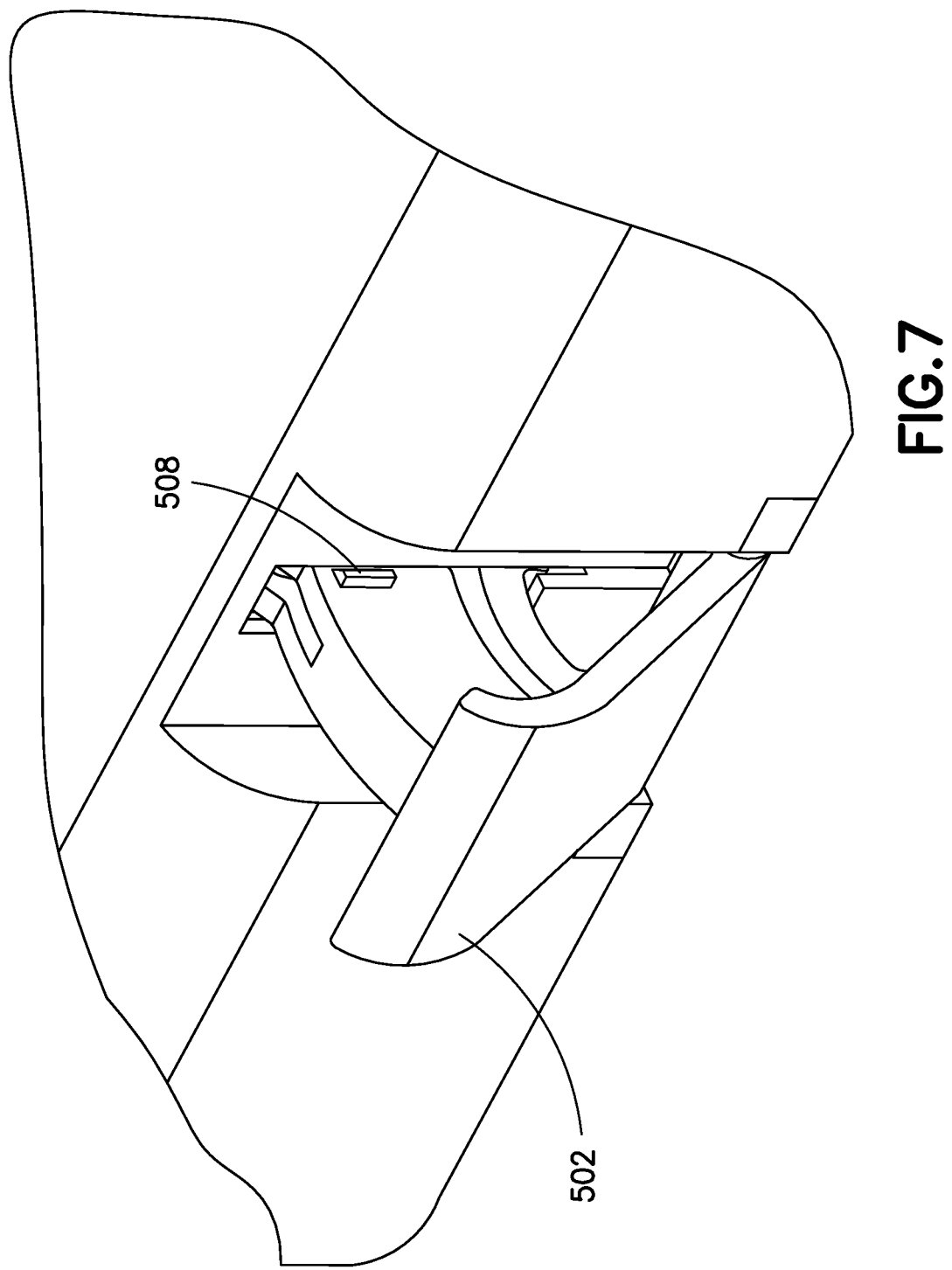
FIG. 7 is an enlarged, partial perspective view of an actuation button of the patch pump of FIG. 5 in the pre-actuated state.

In greater detail, the device 500 includes an actuation button or button 502. According to one embodiment, the button 502 is hingedly connected to a housing having a base 504 (better shown, for example, in FIG. 8). In the pre-actuated stated illustrated in FIG. 5, the button 502 protrudes from the side of a cover 506. As shown in FIG. 7, to ensure that the button is pressed inward with sufficient force (as subsequently described in greater detail), the button 502 preferably includes a set of detents 508 to keep the button 502 in the pre-actuated position until the user applies the desired amount of force to the button 502. Once the desired amount of force has been applied, the detents 508 will deform or deflect (or will deform or deflect the neighboring walls), allowing the user to press the button 502 inward. It will be understood that this feature can also be employed in other embodiments of the present invention and combined with other disclosed features. Although depicted as being located on the button 502, the detents can alternatively be located on the cover 506 adjacent to the button 502. The button, 502, base 504, and cover 506 are preferably made of plastic, such as polypropylene, polyethylene, acrylonitrile butadiene styrene polymers, polyesters such as polyethylene terephthalate or similar materials, and/or bio-based resins such as polylactide, starch-filled polypropylene, or polyhydroxyalkanoates.

Figure 8:
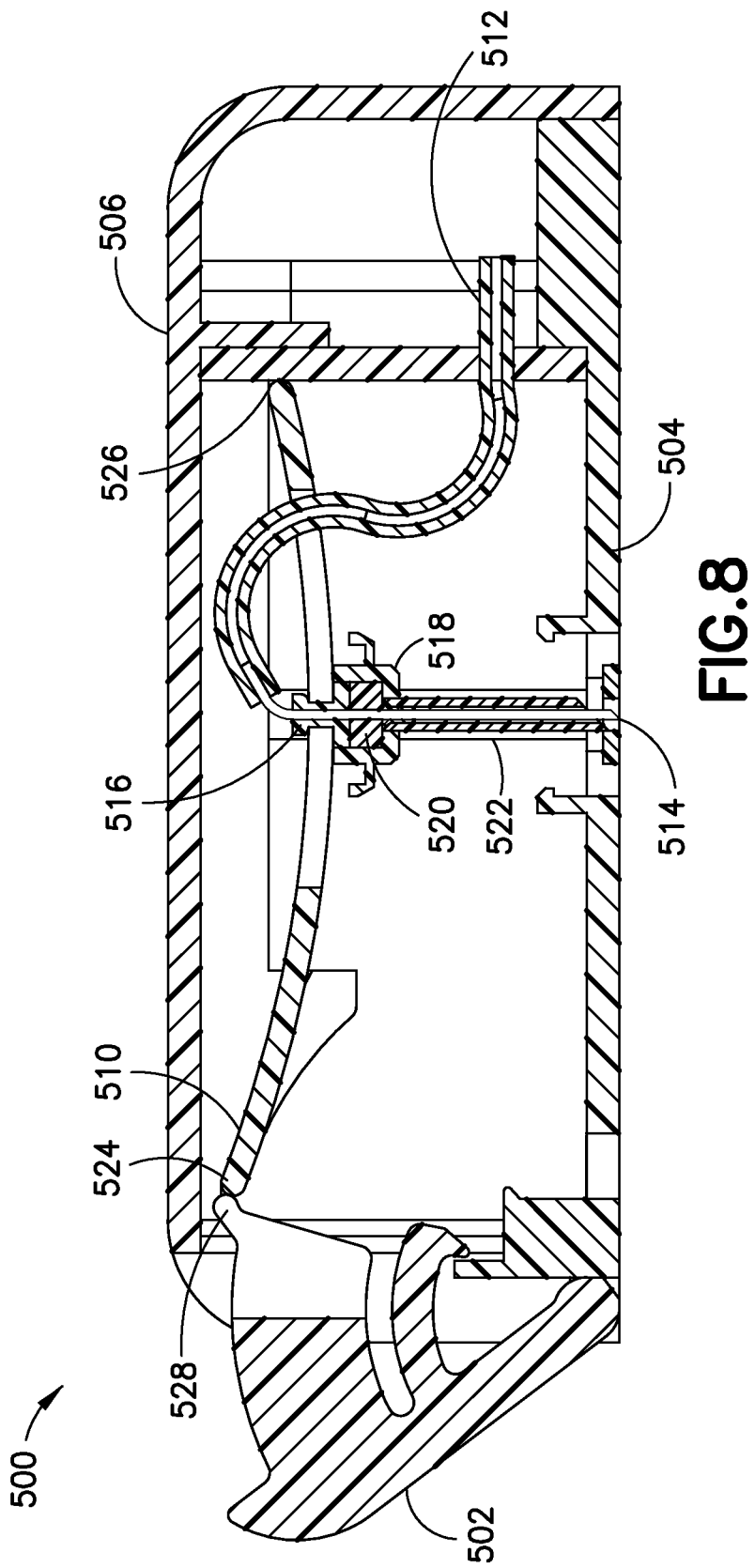
FIGS. 8-11 are cross-sectional views of the operation of the patch pump of FIG. 5.

FIG. 8 is a cross-sectional view of the patch pump 500 in the pre-actuated state. As shown in FIG. 8, the device 500 includes a flexible beam 510, tubing 512 connected to a reservoir (such as reservoir 4) at a first end of the tubing 512 and connected to an insertion needle 514 at a second end of the tubing 512. The insertion needle 514 is preferably made of metal, such as stainless steel, and is hollow. The flexible beam 510 can be made of any suitable material, such as metal or plastic, as long as the dimensions of the beam enable the desired deflection or bending, as subsequently described in greater detail.

According to one embodiment, a cannula carrier 516 secures the insertion needle 514 with the beam 510 to move therewith, and a holder or septum holder or septum and catheter holder 518 is temporarily secured to the distal end of the cannula carrier 516, for example, by an interference fit. According to one embodiment, the carrier 516 fixedly secures the insertion needle 514 with the beam 510. The septum holder 518 has a septum 520 disposed therein and a flexible or soft catheter 522 secured with the septum holder's distal end. According to one embodiment, the septum 520 is fixedly disposed within the septum holder 518 and a flexible catheter 522 is fixedly secured to the septum holder's distal end. In the pre-actuated state of the device 500, the insertion needle 514 extends through the septum 520 and through the distal end of the soft catheter 522.

As shown in FIG. 8, the beam 510 is illustrated in its initial, relaxed state. A second end 526 of the beam 510 is rotatably fixed to the base 504, and in the pre-actuated state of the device 500, a first end 524 of the beam 510 engages or contacts an end 528 of the button 502.

Figure 9:
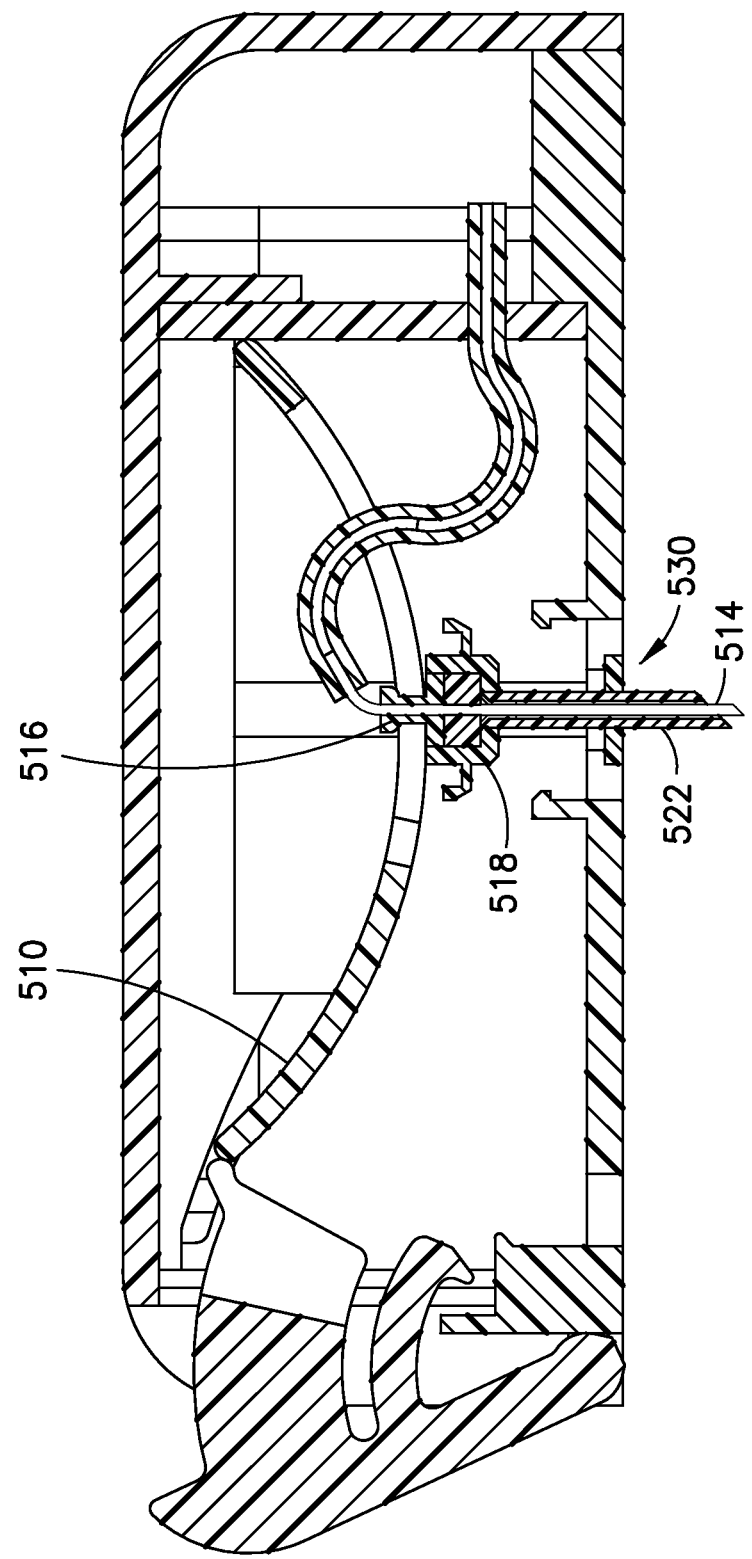

FIG. 9 illustrates an intermediate state in which the user has applied sufficient force to the button 502 to overcome the detents 508, the button 502 has displaced part way through its full travel, and the insertion needle 514 and the soft catheter 522 have extended through an opening 530 in the base 504 outside the patch pump 500 for insertion into the user's skin. In this intermediate state, the force applied to the button bends or deflects the beam 510, and thereby distally displaces the insertion needle 514 and the soft catheter 522 (via the cannula carrier 516 and the septum holder 518). As described subsequently in greater detail, according to one embodiment, the septum holder 518 is constrained to move substantially linearly.

Figure 10:
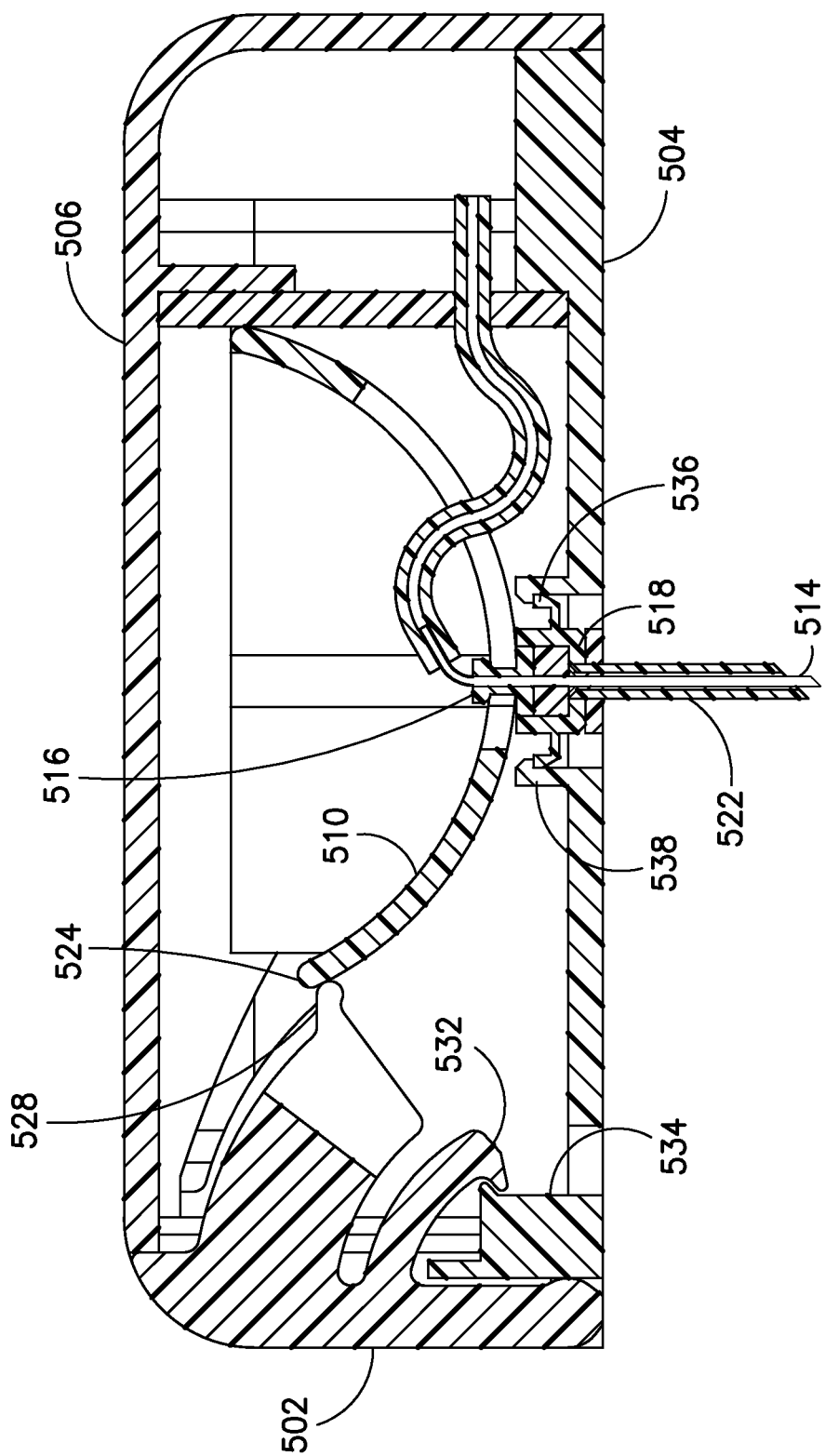

According to one embodiment, as shown in the state illustrated in FIG. 10, the beam has been fully flexed and the insertion needle 514 and the soft catheter 522 have reached a fully-extended position due to the user's force applied to the button 502 to overcome the detents 508. Thus, one skilled in the art will appreciate that the material choice and dimensions of the button 502, the detents 508, and the cover 506 can be selected so that the force required to overcome the detents 508 is substantially equal to or greater than the force required to fully flex the selected material and dimensions of the beam 510 and fully insert the soft catheter 522 and the insertion needle 514.

Also in the state illustrated in FIG. 10, the button 502 has reached its full travel, and is retained in this position by the interaction of a button hook 532 disposed on the button 502 and a button latch 534 disposed on the base 504. At least one of the button hook 532 and the button latch 534 deform during the button travel to achieve this interaction. Additionally, in this state, the septum holder 518 has reached its full travel, and interaction between holder hooks 536 disposed on the holder 518 and holder latches (or snap tabs) 538 disposed on the base maintain the septum holder 518 (and therefore, the soft catheter 522) in this position. It will be understood that these features can also be employed in other embodiments of the present invention and combined with other disclosed features. According to one embodiment, at least one of the holder hooks 536 and the holder latches 538 deform during the septum holder travel to achieve this interaction, which maintains the soft catheter 522 in the fully-extended position.

Figure 11:
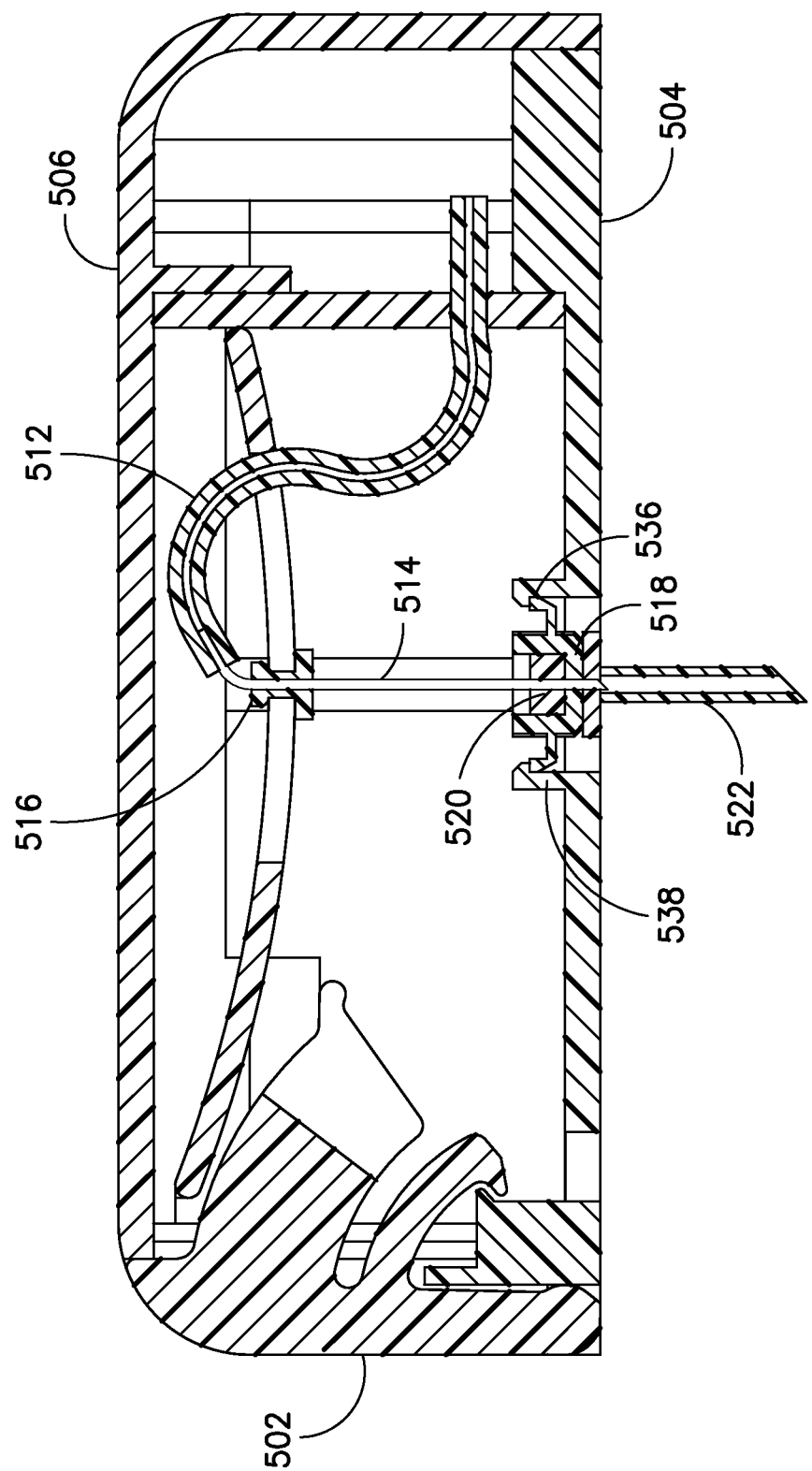

Further, in the state illustrated in FIG. 10, the first end 524 of the beam 510 has slipped past, and out of contact with the end 528 of the button 502. In other words, the first end 524 of the beam 510 has slipped by or disengaged from the end 528 of the button 502. Because the button end 528 is no longer restraining and bending the beam 510, the beam 510 returns to its initial state, as shown in FIG. 11, proximally displacing the cannula carrier 516 (and therefore, the insertion needle 514) relative to the septum holder 518, the septum 520, and the soft catheter 522. Upon return to the beam's initial state, the distal portion of the insertion needle 514 remains in contact with the septum 520 and the distal tip of the insertion needle 514 remains disposed within the proximal end of the soft catheter 522, thereby remaining part of the fluid flow path between the reservoir and the distal end of the soft catheter 522. In other words, the insertion needle 514 remains in the soft catheter 522 and is sealed by the septum 520 to provide a leak-proof fluid path. It will be understood that these features can also be employed in other embodiments of the present invention and combined with other disclosed features.

According to one embodiment, the first end 524 of the beam 510 slips past or disengages from the end 528 of the button 502 substantially simultaneously with the soft catheter 522 and the insertion needle 514 reaching the fully extended position (and the septum holder 518 being maintained by the interaction between the holder hooks 536 and holder latches 538). But the timing of these events can be altered. For example, according to one embodiment, after the soft catheter 522 and the insertion needle 514 reach the fully extended position, the button 502 continues to travel and further flex the beam 510. In this embodiment, it is this further flexure that enables the first end 524 of the beam 510 to slip past the end 528 of the button 502, thereby withdrawing the insertion needle 514 from the fully extended position. An advantage of this embodiment is that the full insertion of the soft catheter 522 is ensured prior to withdrawal of the insertion needle 514. It will be understood that this feature can also be employed in other embodiments of the present invention and combined with other disclosed features.

Figure 12:
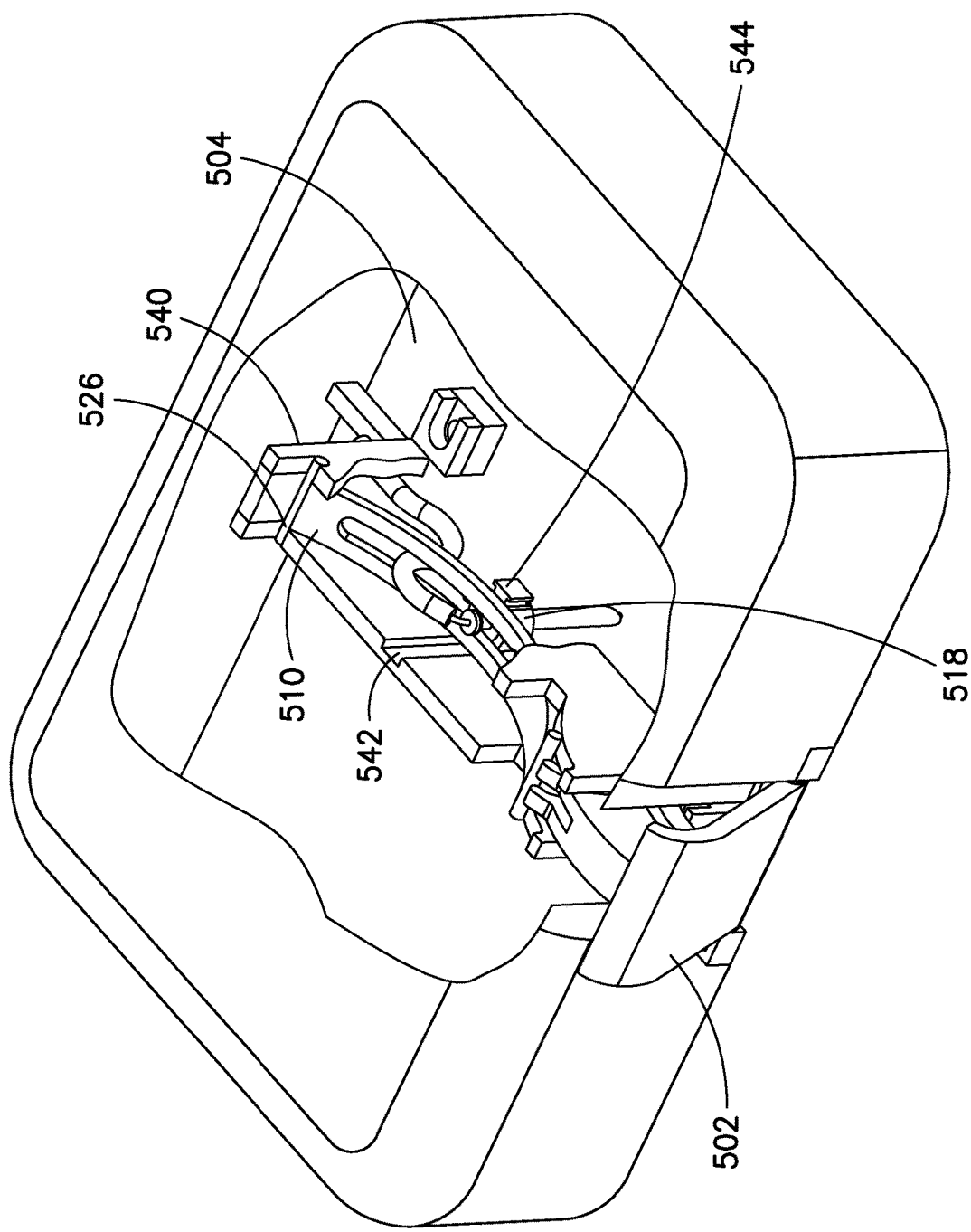
FIG. 12 is a perspective view of the patch pump of FIG. 5 with some portions removed and some portions illustrated as being transparent for clarity.

FIG. 12 is a perspective view of the patch pump 500 with some portions removed and some portions illustrated as being transparent for clarity. One skilled in the art will appreciate that the patch pump components' opacity can vary without departing from the invention's scope. As shown in FIG. 12, the base 504 includes an enclosing structure 540 in which the beam 510 is movably disposed. As previously noted, but best shown in FIG. 12, the second end 526 of the beam 510 is rotatably fixed to the base 504 at the enclosing structure 540. The enclosing structure 540 also includes guide slots 542, which engage and guide tabs 544 that extend from the septum holder 518 to ensure that the travel of the septum holder (and thus, the insertion needle 514 and the soft catheter 522) is substantially linear, and substantially perpendicular to the distal surface (patient contact surface) of the base 504.

Figure 13:
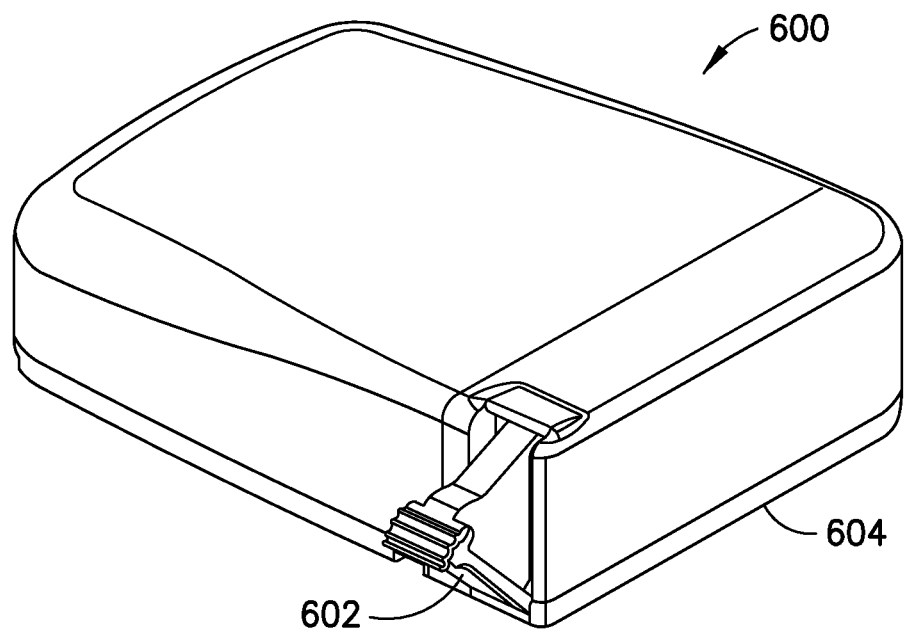
FIGS. 13 and 14 are perspective views of a patch pump in respective pre-actuated and actuated states in accordance with another embodiment of the present invention.
Figure 14:
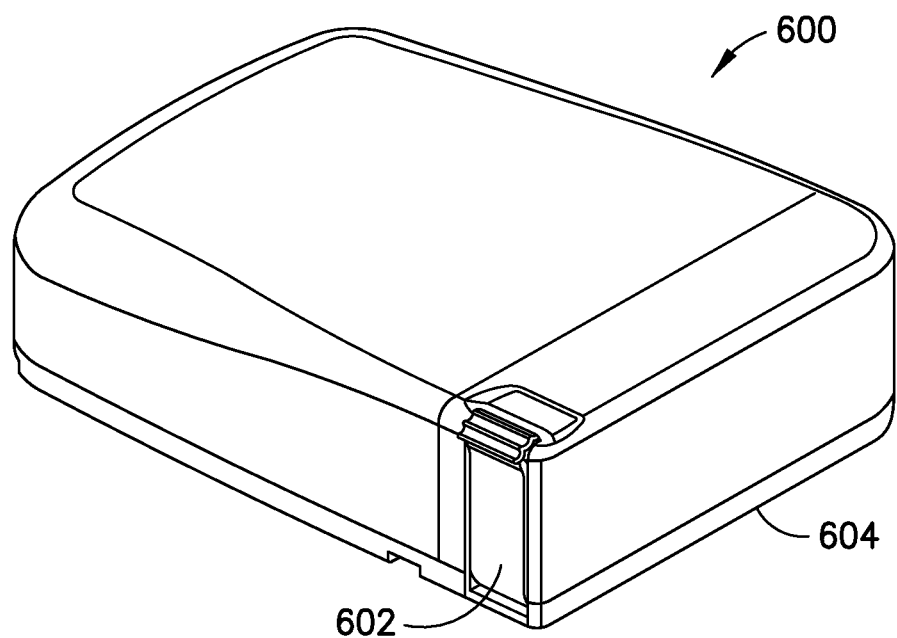

As shown in FIGS. 5 and 6, in one embodiment, the button 502 is located substantially in the middle of the patch pump 500. According to another embodiment, as shown in FIGS. 13 and 14, the button 602 (along with the beam, insertion needle, etc.) can be disposed at an end of the patch pump 600. It will be understood that this feature can also be employed in other embodiments of the present invention and combined with other disclosed features. By moving the catheter insertion mechanism to one end of the device, the remainder of the space in the device can be used to efficiently contain the rest of the device's components (electronics, pump, batteries, reservoir, circuitry, etc.).

Figure 15:
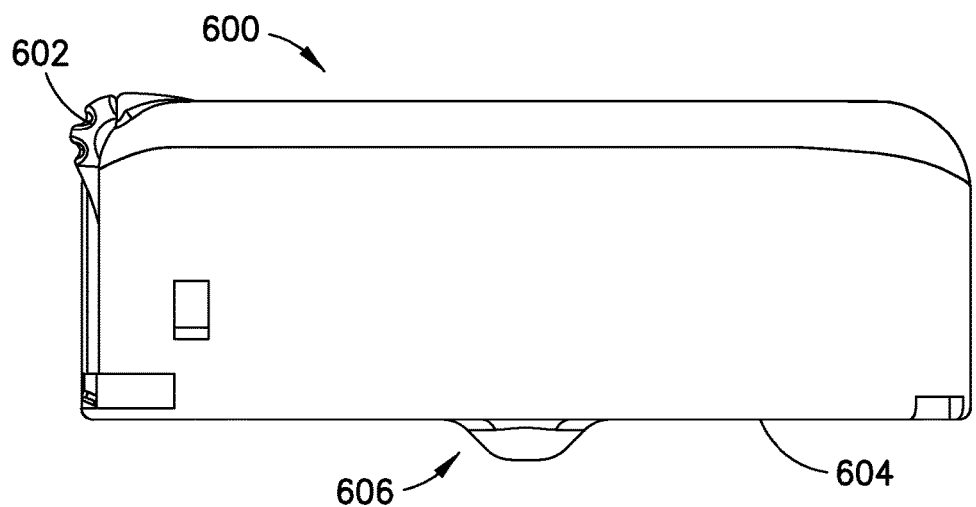
FIG. 15 is a side view of the patch pump of FIG. 13.

In addition, as illustrated in FIG. 15, the base 604 includes a small protrusion 606, which provides more space in the interior of the device 600 to house the catheter insertion mechanism. It will be understood that this feature can also be employed in other embodiments of the present invention and combined with other disclosed features. Preferably, the protrusion 606 is small enough to prevent the user from being able to sense its presence. Moreover, the protrusion 606 stretches the user's skin to improve penetration of the insertion needle and reduces the likelihood of skin tenting at the opening in the base 604 that the soft catheter 622 extends through.

Figure 16:
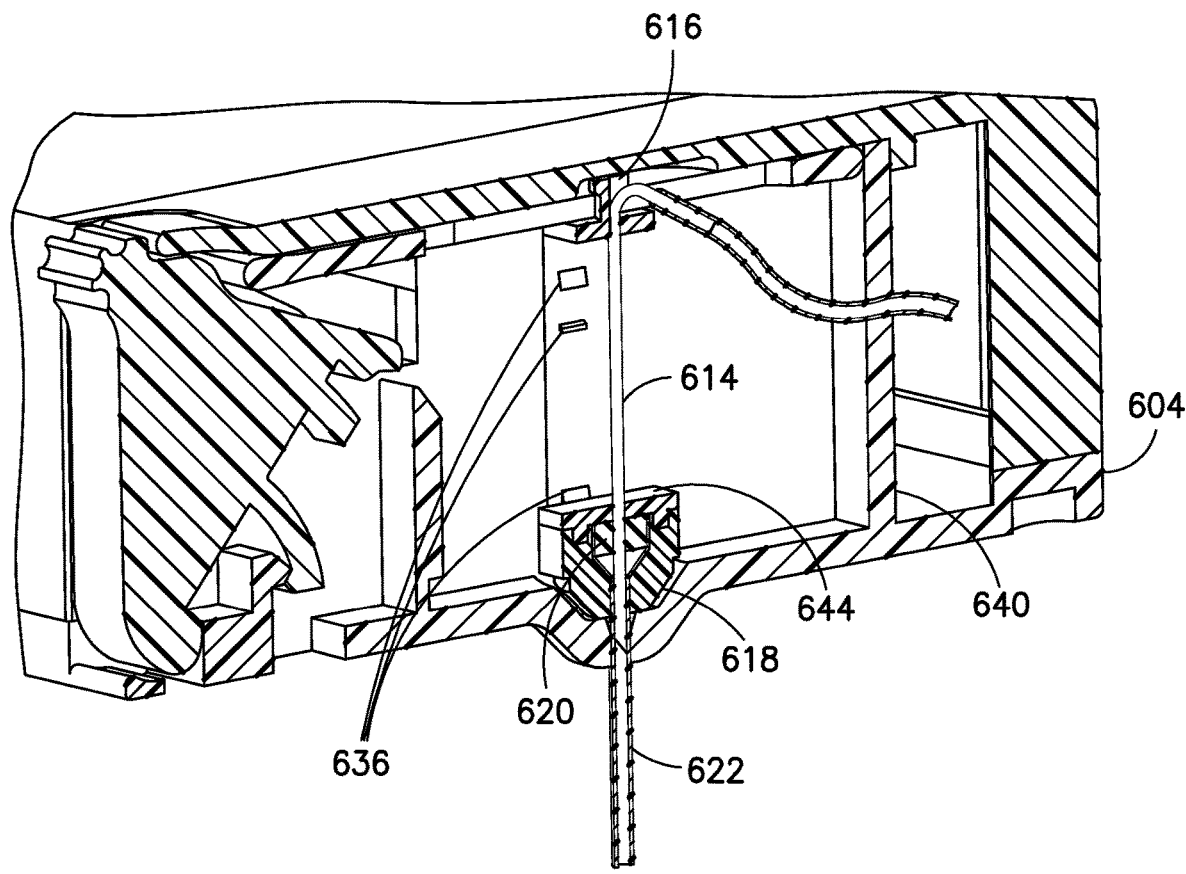
FIG. 16 is a perspective cross-sectional view of the patch pump of FIG. 13.
Figure 17:
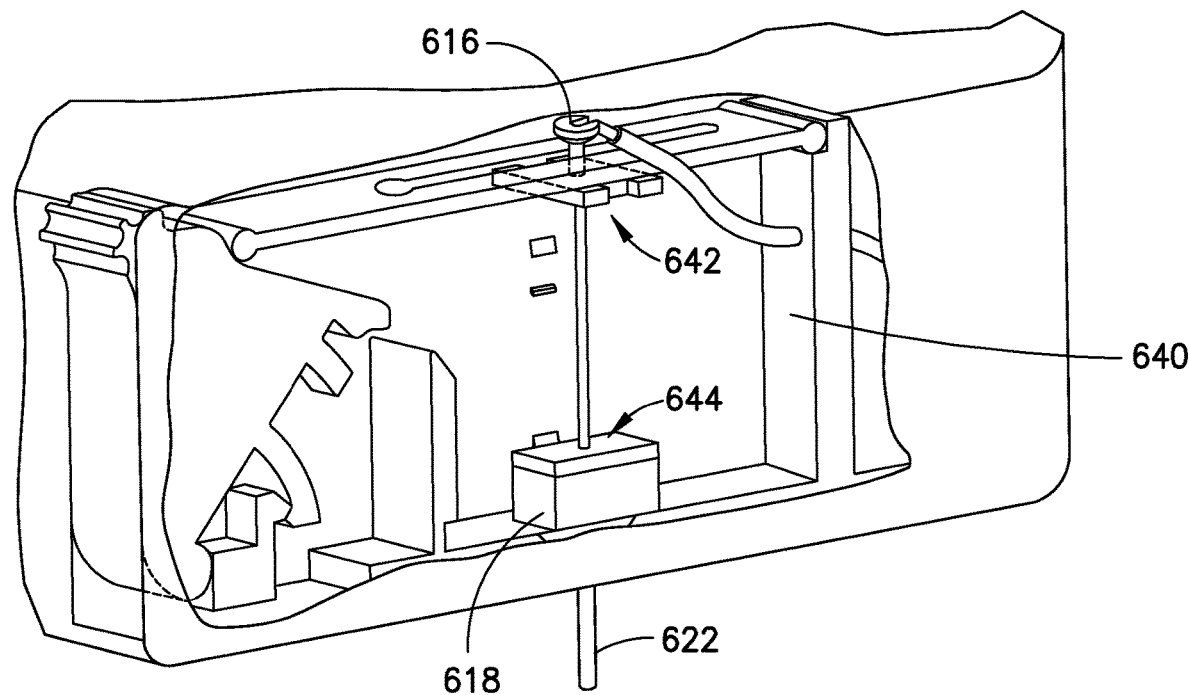
FIG. 17 is a perspective view of the patch pump of FIG. 13 illustrated with a transparent cover for clarity.

FIG. 16 is a perspective cross-sectional view of the patch pump 600, and FIG. 17 is a perspective view of the patch pump 600 illustrated with a transparent cover for clarity.

Figure 18:
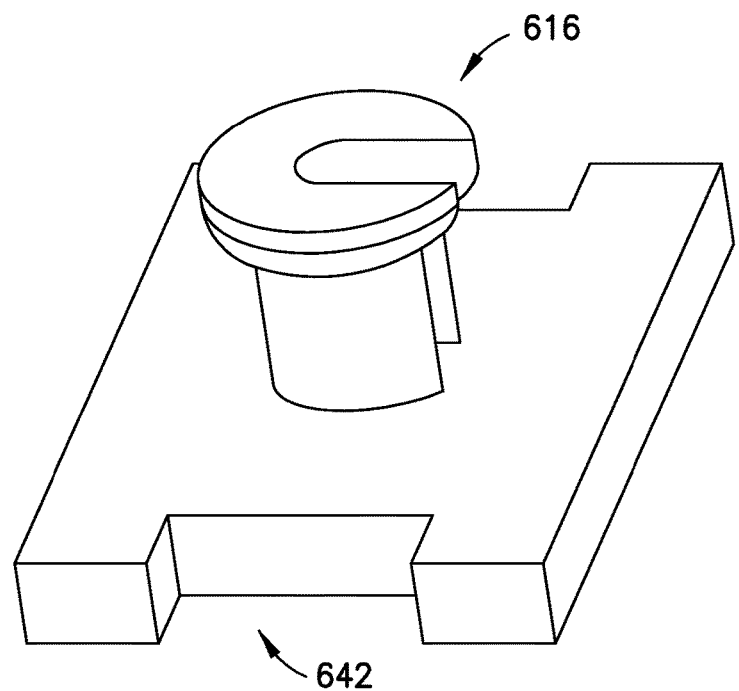
FIG. 18 is a perspective view of a cannula holder of the patch pump of FIG. 13.

In contrast to the patch pump 500, instead of using holder hooks and holder latches to maintain the catheter 622 in the fully-extended position, a series of small bumps or detents 636, as shown in FIGS. 16 and 17, are disposed on the interior of the enclosing structure 640. These bumps or detents 636 maintain the holder or septum and catheter holder 618 in the pre-actuation and fully-extended positions. The cannula holder 616, shown best in FIG. 18, is connected with the flexible beam 610, and includes notches 642 so that the cannula holder 616 can pass by the bumps 636 during the insertion needle 614 insertion and retraction. It will be understood that this feature can also be employed in other embodiments of the present invention and combined with other disclosed features.

Additionally, in the patch pump 600, a small cap 644 is secured to the top of the septum and catheter holder 618 to prevent the septum 620 from pulling out of the septum and catheter holder 618 during the insertion needle's retraction. According to one embodiment, the cap 644 is adhered to the septum and catheter holder 618.

Figure 19:
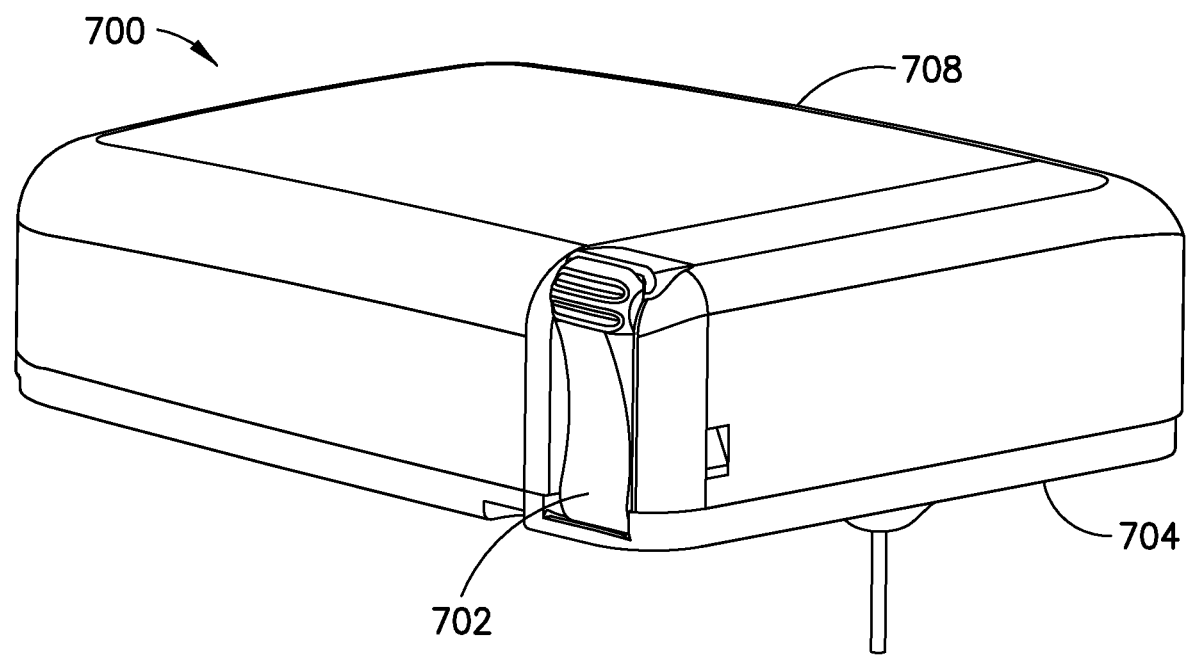
FIG. 19 is a perspective view of a patch pump in an actuated state in accordance with another embodiment of the present invention.
Figure 20:
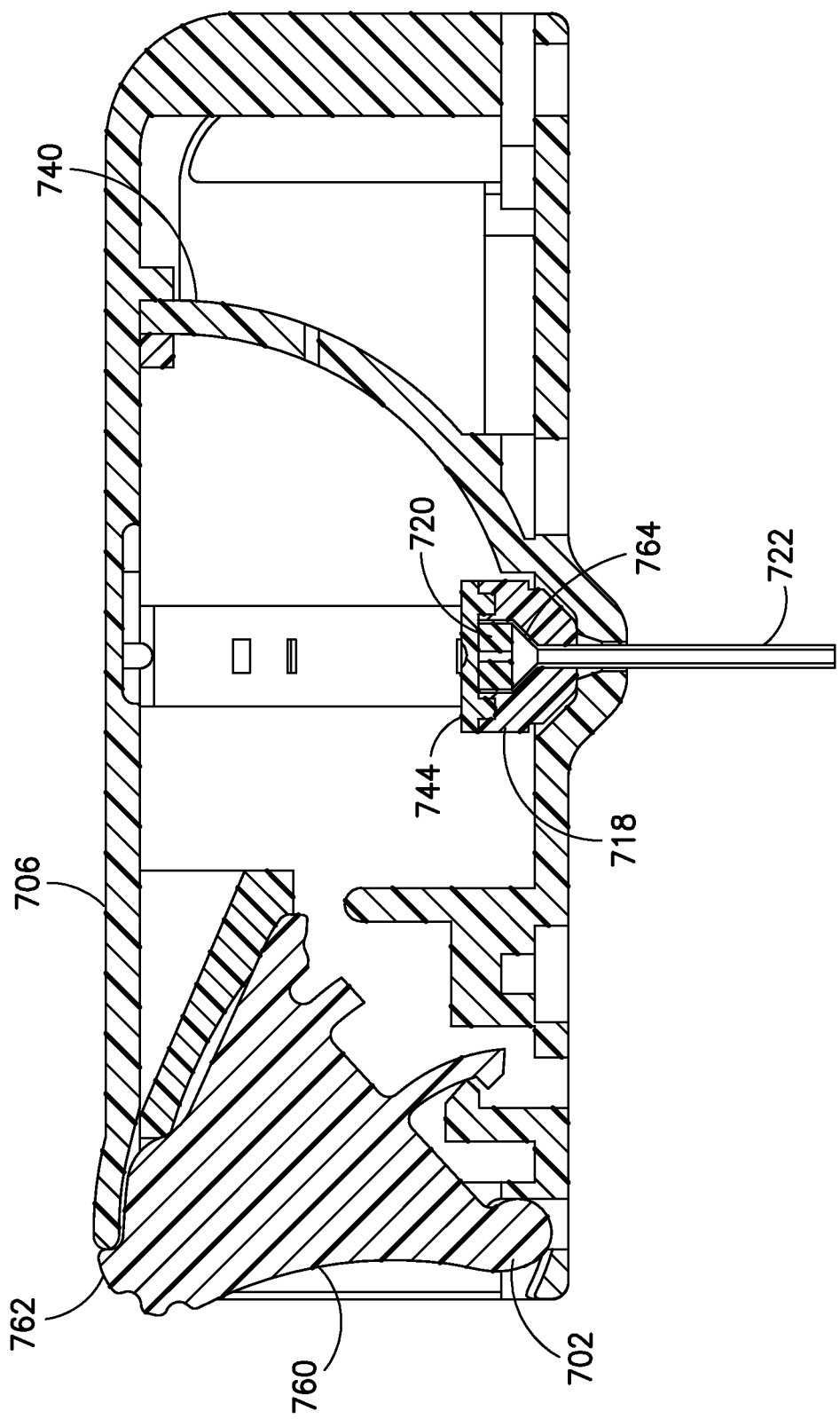
FIG. 20 is a cross-sectional view of the patch pump of FIG. 19 with several elements omitted for clarity.
Figure 21:
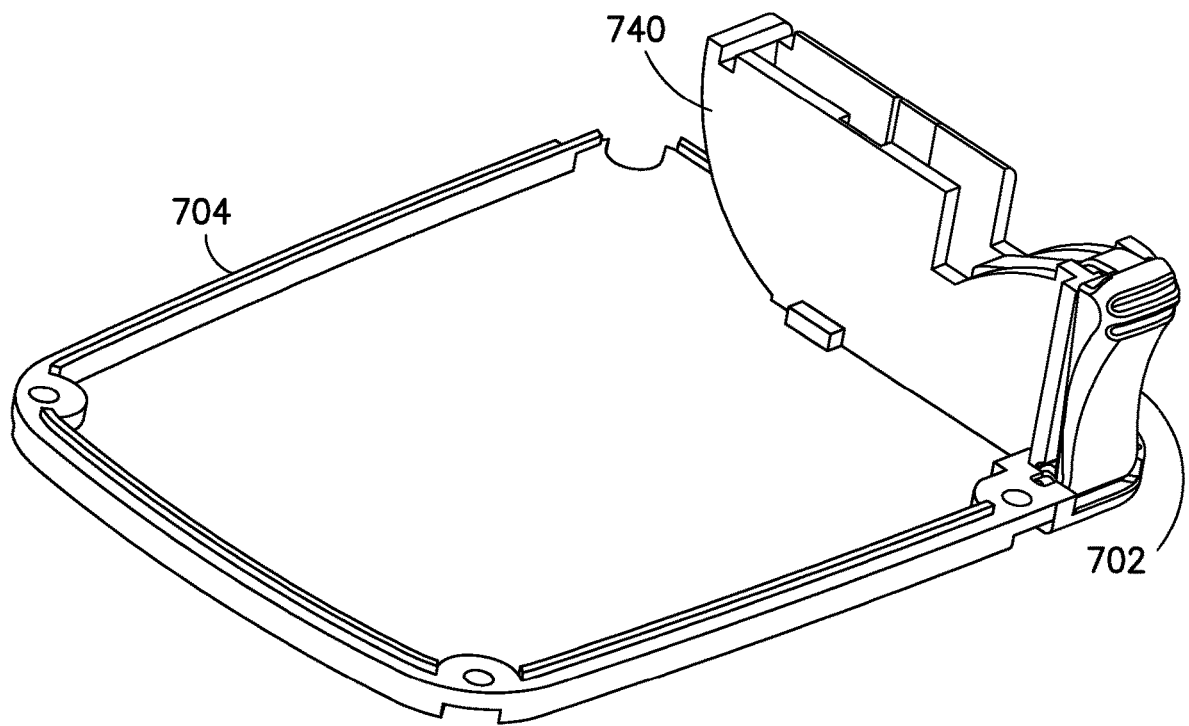
FIG. 21 is a rear perspective view of the patch pump of FIG. 19 with several elements removed for clarity.

FIG. 19 is a perspective view of a patch pump 700 in an actuated state in accordance with another embodiment of the present invention. FIG. 20 is a cross-sectional view of the device 700, and FIG. 21 is a rear perspective view of the device 700. In FIGS. 20 and 21, several elements are omitted for clarity, such as the flexible beam 710, which is substantially the same as the flexible beam 610. As shown in FIG. 19, the top corners of cover 706 are more rounded than in previously-described embodiments. This feature makes it less likely that the path pump 700 might catch on a user's clothes when in use.

As shown in FIGS. 19-20, the button 702 has a different external profile than previously-described embodiments. More specifically, the side 760 of the button 702 is curved to be concave, and this "scoop out" in the lower portion of the button 702 is located closer to the button's pivot point. Positioning the "scoop out" in this location, forces the user to push on the button portion farthest from the pivot point (the portion with grips or ridges 762). This increases the torque on the button during activation which ensures consistent and full activation In other words, this shape encourages user to press the button 702 at or at least closer to the grips 762 than previously-described embodiments, to more easily apply the force necessary to overcome the detents. It will be understood that this feature can also be employed in other embodiments of the present invention and combined with other disclosed features.

Additionally, as shown in FIGS. 20 and 21, the side of the enclosing structure 740 opposite to the button 702 is curved. This shape provides more usable volume inside the cover for the other systems of the patch pump 700. Put another way, the modified enclosing structure 740 creates room for other internal components. For example, additional components can be disposed under and adjacent to the curved surface.

Figure 22:
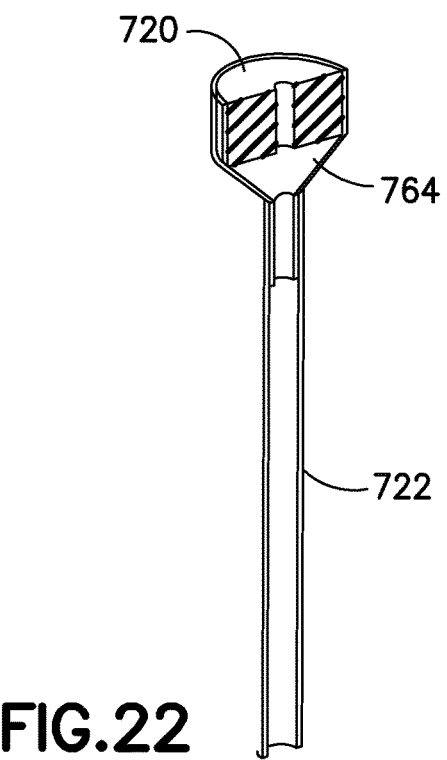
FIG. 22 is a cross-sectional view of a soft catheter and wedge for use in embodiments of the present invention.

As shown in FIGS. 20 and 22, the soft catheter 722 is secured to the holder or septum and catheter holder 718 using a wedge 764, and the septum 720 is secure to the inside of the wedge 764. More specifically, the proximal portion of the soft catheter 722 fits around the distal end of the wedge 764, and that subassembly is secured through an opening in the septum and catheter holder 718 to fixedly connect the soft catheter 722 with the septum and catheter holder 718. Although only described with respect to the patch pump 700, a wedge can be used to secure the catheter in any of the embodiments, and like the other described features, can be combined with features of other embodiments without departing from the present invention's scope.

Embodiments of the present invention only require a user to perform a single operation (depressing the button) to both insert the soft catheter and retract the introducer needle. In one embodiment, no other interaction with the device is needed for catheter deployment and the initiation of medicament delivery. In another embodiment, subsequent to placement of the patch pump on the patient's skin and dosage setting, for example, by a remote device, the only required user interaction with the patch pump to insert the soft catheter, retract the introducer needle, and begin medicament delivery is to depress the button.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. A catheter insertion device, comprising:
   a. a housing having a base;
   b. a flexible beam movably disposed within the housing;
   c. an insertion needle connected with the beam;
   d. a holder movably disposed within the housing and movably connected with the insertion needle;
   e. a catheter connected with the holder to displace therewith, the catheter surrounding at least a portion of the insertion needle; and
   f. an actuator button movably connected to the housing;
   g. wherein in a pre-actuated state of the device, the actuator button contacts a free, first end of the beam, a second end of the beam being connected to the housing, and the beam is in a relaxed state; and
   h. wherein the actuator button is configured to increase flexion of the beam upon actuation, thereby displacing the insertion needle and the catheter to an extended position in which respective distal portions of the insertion needle and the catheter extend outside the housing through the base.

2. The device according to claim 1, wherein one of upon or subsequent to the insertion needle and the catheter reaching the extended position, the free end of the beam moves past a contact portion of the actuator button and disengages from the actuator button, and the beam returns to the relaxed state, thereby withdrawing the insertion needle from the extended position.

3. The device according to claim 1, further comprising a reservoir for containing a medicament;
   wherein subsequent to the insertion needle returning to an initial position, a fluid path between the reservoir and a distal end of the catheter comprises the insertion needle.

4. The device according to claim 1, further comprising a locking feature locking the holder upon the catheter reaching the extended position.

5. The device according to claim 4, further comprising:
   a cannula carrier fixedly connected to the beam and securing the insertion needle to the beam;
   wherein the locking feature comprises a detent disposed on the housing permitting the holder to travel past the detent in a single direction; and
   wherein the cannula carrier has a cutout permitting the cannula carrier to travel past the detent in multiple directions.

6. The device according to claim 4, wherein the locking feature comprises a snap disposed on the base and configured to non-releasably engage an arm of the holder upon the catheter reaching the extended position.

7. The device according to claim 1, wherein one of the holder and the housing includes a guide and a remaining one of the holder and the housing includes a guide track; and interaction of the guide and the guide track confines motion of the catheter.

8. The device according to claim 7, wherein the housing includes the guide track and the holder includes the guide confining motion of the catheter.

9. The device according to claim 1, wherein the base includes a protrusion extending outward around an opening through which the catheter extends.

10. The device according to claim 1, further comprising a septum disposed in the holder and through which the insertion needle is movably disposed.

11. The device according to claim 1, wherein the actuator button is rotatably fixed to a side of the housing.

12. The device according to claim 1, wherein the actuator button comprises:
    a gripping portion; and
    a concave portion adjacent to a button rotational axis to direct an actuation force of a user to be applied closer to the gripping portion than to the rotational axis.

13. The device according to claim 1 further comprising:
    a detent disposed on one of the actuator button and the housing;
    wherein a user actuation force to overcome the detent and move the actuator button relative to the housing is not less than a force required to flex the beam and move the catheter to the extended position.

14. A method of inserting a cannula disposed on a holder, the cannula being disposed about an insertion needle connected to a beam disposed inside a medical device housing, the method comprising:
    increasing deflection of the beam by displacement of an actuator button relative to the housing until the cannula and the insertion needle reach an extended position outside the housing, and the holder and the actuator button lock to the housing.

15. A catheter insertion device, comprising:
    a housing having a base;
    a cantilevered, flexible beam movably disposed within the housing and having a free end;
    an insertion needle connected with the beam;
    a holder movably disposed within the housing and movably connected with the insertion needle;
    a catheter connected with the holder to displace therewith, the catheter surrounding at least a portion of the insertion needle; and
    an actuator button movably connected to the housing and having an end, the end being configured to, upon actuation, remain in direct contact with the free end of the beam to increase flexion of the beam, until the insertion needle and the catheter are moved to an extended position in which respective distal portions of the insertion needle and the catheter extend outside the housing through the base;
    wherein the end of the actuator button is configured to, upon the insertion needle and the catheter reaching the extended position, continue to move past the free end of the beam and disengage from the beam; and
    wherein subsequent to the end of the actuator button moving past the free end of the beam, the beam is configured to return to an initial beam position, thereby withdrawing the insertion needle from the extended position and ensuring full insertion of the catheter prior to withdrawal of the insertion needle.

16. A catheter insertion device, comprising:
    a housing having a base;
    a flexible beam movably disposed within the housing;
    an insertion needle connected with the beam;
    a holder movably disposed within the housing and movably connected with the insertion needle;
    a catheter connected with the holder to displace therewith, the catheter surrounding at least a portion of the insertion needle; and
    an actuator button movably connected to the housing and configured to, upon actuation, increase flexion of the beam until the insertion needle and the catheter reach their full travel, in which respective distal portions of the insertion needle and the catheter extend outside the housing through the base;

wherein the actuator button is configured to, upon the insertion needle and the catheter reaching an extended position, lock to the housing; and wherein the beam is configured to, subsequent to the insertion needle and the catheter reaching the extended position, disengage from the actuator button and return to an initial beam position, thereby withdrawing the insertion needle from the extended position and ensuring full insertion of the catheter prior to withdrawal of the insertion needle.

17. The device according to claim 16, wherein the actuator button is configured to disengage from the beam subsequent to the insertion needle and the catheter reaching their full travel.

* * * * *